United States Patent [19]

Müller

[11] 4,046,777
[45] Sept. 6, 1977

[54] FLUORINE SUBSTITUTED MALEIMIDES

[75] Inventor: Albrecht Müller, Allschwil, Switzerland

[73] Assignee: Ciba-Geigy Corporation, Ardsley, N.Y.

[21] Appl. No.: 610,515

[22] Filed: Sept. 3, 1975

[30] Foreign Application Priority Data

Sept. 19, 1974 Switzerland .................. 12722/74

[51] Int. Cl.$^2$ .......................................... C07D 207/12
[52] U.S. Cl. .................. 260/326.26; 260/326.5 FM; 260/518 A; 260/78 UA
[58] Field of Search ............... 260/326.26, 326.5 FM, 260/518 A, 78 AU

[56] References Cited

U.S. PATENT DOCUMENTS 3,660,408  5/1972  Ackerman ............... 260/326.5 FM

Primary Examiner—Lewis Gotts
Assistant Examiner—Cary Owens
Attorney, Agent, or Firm—Luther A. R. Hall

[57] ABSTRACT

Fluorine-containing maleic and derivative of the formula

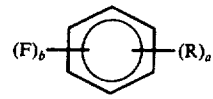

wherein a denotes 1 or 2 and R denotes either the radical —NH·CO—D—CO·OH or the radical

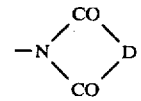

wherein D represents a divalent radical containing a carbon-carbon double bond, and in which $b$ denotes a number from 3 to 5 if $a = 1$, or b denotes 3 or 4 if $a = 2$, and if $a = 2$ the two radicals R are preferably in the p- or in the m-position to one another, are prepared.

These compound are useful for preparing high polymers with good heat resistance.

4 Claims, No Drawings

FLUORINE SUBSTITUTED MALEIMIDES

The invention relates to new maleimides containing fluorine, the corresponding maleamic acids which arise as intermediate products in the manufacture of these maleimides, and the use of the maleimides and maleamic acids, containing fluorine, for the manufacture of high polymers.

Maleimides have in recent years attained considerable importance as starting materials for the manufacture of high polymers. They can be polymerised, by themselves or in combination with other suitable monomers, by warming or catalytically. The polyaddition reaction of polymaleimides with organic polyamines or polythiols is also known. In this context, attention should be drawn to French Patent 1,555,564 and U.S. Pat. No. 3,741,942. However, the high polymers thus obtainable still suffer from considerable disadvantages. In particular, they will not withstand exposure to high temperatures or even moderate temperatures.

The task of the invention is to provide new maleic acid derivatives, containing fluorine, which can be employed as starting materials for the manufacture of particularly heatresistant high polymers.

The subject of the invention are maleic acid derivatives, containing fluorine, of the formula I

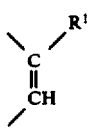

(I)

in which a denotes 1 or 2 and R denotes either the radical —NH·CO—D—CO·OH or the radical

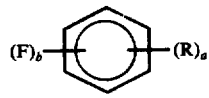

wherein D represents a divalent radical containing a carboncarbon double bond, and in which b denotes a number from 3 to 5 if $a = 1$, or b denotes 3 or 4 if $a = 2$, and if $a = 2$ the two radicals R are preferably in the p- or in the m-position to one another.

D in the radical R preferably denotes a divalent radical of the formula II

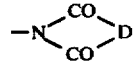

(II)

in which $R^1$ repesents hydrogen or methyl. According to the invention, particular importance attaches to pure maleic acid derivatives, that is to say to $R^1$ being hydrogen in the formula II.

The most important, and industrially most interesting, of the maleic acid derivatives according to the invention are the following compounds:

(III)

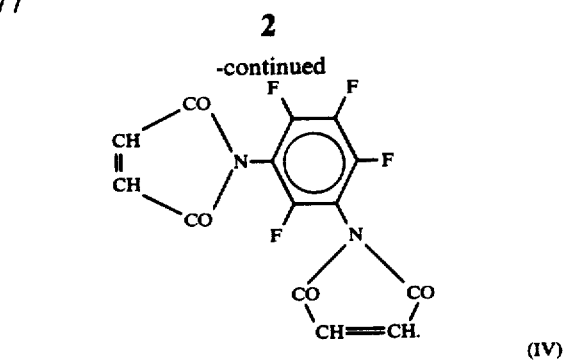

(IV)

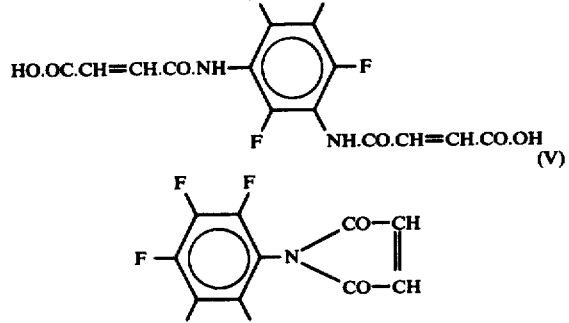

(V)

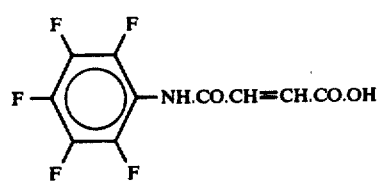

and (VI)

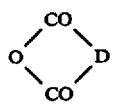

The compounds according to the invention are manufactured by the reaction of an amine of the formula VIII (VIII)

with an acid anhydride of the formula IX (IX)

$$\begin{array}{c} CO \\ O \diagup \diagdown D \\ \diagdown CO \diagup \end{array}$$

in the equivalent ratio of amine to anhydride of $\leq 1:1$, preferably in the stoichiometric ratio. The reaction takes place in 2 stages. The 1st stage is carried out in the presence of organic solvents at temperatures of, preferably, $-10°$ to $+50°$ C. This gives the amidocarboxylic acid, according to the invention, of the formula X (X)

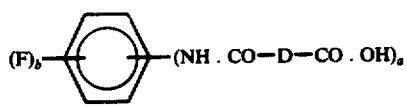

which can be isolated by removing the solvent and can be used, as such, for the manufacture of high polymers.

The resulting product of the formula X can, however, also be subjected to a cyclising dehydration in a 2nd stage. This is carried out in the presence of low, dehydrating carboxylic acid anhydrides, catalysts and tertiary amines and in the presence or absence or organic solvents. The end product obtained is the monomaleimide or dimaleimide according to the invention, of the formula VII

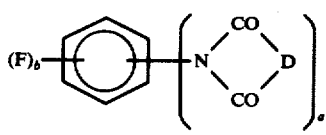

(VII)

Possible amines of the formula VIII which can be used for the manufacture of the products according to the invention are, in particular, tetrafluoro-m-phenylenediamine and pentafluoroaniline.

As regards the 2nd stage (cyclising dehydration) practically the same applies, in other respects, as applies to the manufacture of known maleimides using halogen-free amines as starting materials. This means that a suitable lower, dehydrating, carboxylic acid anhydride is in particular acetic anhydride. Suitable catalysts for the cyclising dehydration are soluble nickel salts and alkaline earth metal compounds, such as calcium acetate, calcium oxide, barium acetate, barium oxide and strontium oxide. Suitable tertiary amines are trialkylamines, especially triethylamine and N,N-dialkylbenzylamines with 1 to 12 C atoms.

A further subject of the invention are corresponding storage-stable, hot-curable mixtures A which are suitable for the production of mouldings, impregnations, coatings, foams, adhesive bonds and the like and which are characterised in that they contain a. maleic acid derivatives of the formula XI

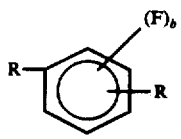

(XI)

in which R denotes either the radical —NH·CO—D—CO·OH or the radical

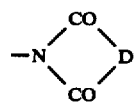

wherein D represents a divalent radical containing a carbon-carbon double bond, b denotes 3 or 4 and the two radicals R are preferably in the p- or m-position to one another, b. primary, preferably halogen-substituted polyamines or polyhydric alcohols or polyhydric phenols or polycarboxylic acids or mixtures of the three last-mentioned compounds with polyamines and optionally c. additionally, basic catalysts, in a ratio such that per 1 equivalent of maleic acid derivative of the formula XI there are 0.1 to 1.5 equivalents of primary polyamine or polyhydric alcohol or polyhydric phenol or polycarboxylic acid or of the mixture of one of the three last-mentioned compounds with polyamine, and that there are 0.01 to 15 parts by weight of basic catalyst per 100 parts by weight of all reactive components.

Maleic acid derivatives particularly suitable for these mixtures A are the compounds of the formulae III and IV.

Primary polyamines particularly suitable for the mixtures according to the invention are C1-substituted and F-substituted aromatic diamines such as, for example, tetrafluoro- and tetrachloro-m-phenylenediamine.

Further primary amines suitable for the mixtures according to the invention include non-halogenated aromatic or araliphatic di- or tri-primary amines with 2 to 40 C atoms in the molecule. Diamines of the formula XII

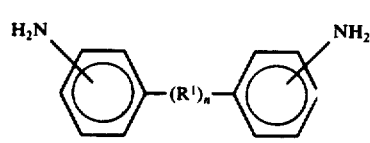

(XII)

in which $R^1$ and $n$ have the abovementioned meaning are particularly suitable.

In principle it is also possible to employ all the polyamines which have already been listed in French Patent 1,555,564. Individually, the following polyamines suitable for the process according to the invention may be mentioned: 1,2,4-triaminobenzene, 1,3,5-triaminobenzene, 2,4,6-triaminotoluene, 2,4,6-triamino-1,3,5-trimethylbenzene, 1,3,7-triaminonaphthalene, 2,4,4'-triaminodiphenyl, 3,4,6-triaminopyridine, 2,4,4'-triaminophenyl ether, 2,4,4'-triaminodiphenylmethane, 2,4,4'-triaminodiphenylsulphone, 2,4,4'-triaminobenzophenone, 2,4,4'-triamino-3-methyldiphenylmethane, N,N,N-tri-(4-aminophenyl)-amine, tri-(4-aminophenyl)-methane, tri-(4-aminophenyl) phosphate, tri-(4-aminophenyl) phosphite, tri-(4-aminophenyl) thiophosphate, 3,5,4'-triaminobenzanilide, melamine, 3,5,3',5'-tetraaminobenzophenone, 1,2,4,5-tetraaminobenzene, 2,3,6,7-tetraaminonaphthalene, 3,3'-diaminobenzidine, 3,3',4,4'-tetraaminophenyl ether, 3,3',4,4'-tetraaminodiphenylmethane, 3,3',4,4'-tetraaminodiphenylsulphone, 3,5-bis-(3,4'-diaminophenyl)-pyridine, 4,4'-diaminodicyclohexylmethane, 1,4-diaminocyclohexane, m-phenylenediamine, p-phenylenediamine, 4,4'-diaminodiphenylmethane, bis(4-aminophenyl)-2,2-propane 4,4'-diaminodiphenyl ether, 4,4'-diaminodiphenylsulphone, 1,5-diaminonaphthalene, m-xylylenediamine, p-xylylenediamine, ethylenediamine, hexamethylenediamine, bis-(γ-aminopropyl)-5,5-dimethylhydantoin and 4,4'-diaminotriphenyl phosphate.

For the sake of detail it should be mentioned that polyamines which are obtained by reaction of primary aromatic amines with aldehydes or ketones are also suitable. In this respect, attention should be drawn to French Patent Specifications 1,430,977 and 1,481,932.

Polyhydric alcohols to be mentioned as suitable (optionally as a mixture of different alcohols) as components for the mixtures according to the invention are, in particular, dihydric or trihydric alcohols.

Unbranched or branched aliphatic alcohols with a total of 2 to 12 C atoms, such as, for example, ethylene glycol, 1,3-propanediol, 1,4-butanediol, 1,5-pentanediol, 1,6-hexanediol, 1,8-octanediol, 1,2,6-hexanetriol, 1,1,1-trishydroxymethylpropane and glycerol are suitable. Alcohols which contain one or more olefinic double bonds are also suitable in principle.

Cycloaliphatic or cycloaliphatic-aliphatic alcohols with 1 or more cycloaliphatic nuclei, which can optionally contain oxygen, sulphur or sulphur-containing radicals as binder members and wherein the hydroxyl groups are bonded either to the aliphatic or to the cycloaliphatic radicals are also suitable components.

Particular attention should also be drawn to compounds which correspond to the formula XIII

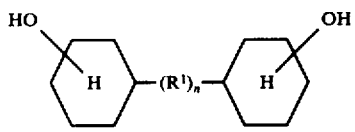

in which R¹ denotes one of the radicals —CH₂—,

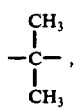

—SO₂—, —SO—, —S—and —O—and $n$ is 0 or 1.

Examples of such compounds are hydrogenated bisphenol A, bis-(p-hydroxycyclohexyl)-methane, bis-(p-hydroxycyclohexyl)-sulphone, bis-(p-hydroxycyclohexyl)-sulphoxide, bis-(p-hydroxycyclohexyl)-sulphide, bis-(p-hydroxycyclohexyl) ether and 4,4'-dihydroxy-dicyclohexyl.

Further alcohols which are very suitable for the mixtures according to the invention are polyglycol ethers of polyhydric alcohols or phenols such as, for example, the diglycol ethers of the abovementioned compounds of the formula XIII, especially bisphenol-A diglycol ethers.

Further suitable cycloaliphatic-aliphatic alcohols which should be mentioned are polymethylol compounds such as, for example, cyclohexanedimethylol. The simplest of the purely cycloaliphatic alcohols which can be employed as a component of the mixture is 1,4-cyclohexanediol.

Polyhydric phenols to be mentioned, which (optionally as a mixture of different phenols) are suitable constituents of the mixtures according to the invention are both mononuclear phenols such as hydroquinone, hydroxyhydroquinone, pyrogallol, phloroglucinol, pyrocatechol and resorcinol, and polynuclear phenols. Such polynuclear phenols are, for example, compounds of the formula XIV

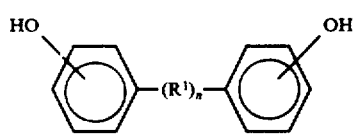

in which R¹ and $n$ have the meaning already mentioned above. In particular, bisphenol A should be mentioned in this context. Further compounds which correspond to this formula XIV are bis-(p-hydroxyphenyl)-methane, bis-(p-hydroxyphenyl)-sulphone, bis-(p-hydroxyphenyl)-sulphoxide, bis-(p-hydroxyphenyl)-sulphide, bis-(p-hydroxyphenyl) ether and 4,4'-dihydroxydiphenyl. In principle, the mixture can also contain polynuclear phenols in which the hydrogen atoms of the nucleus are partly replaced by halogen atoms. Tetrabromobisphenol A may be mentioned as an example.

Other types of polynuclear polyphenols which are suitable for the mixtures according to the invention are those compounds which contain fused rings. 1,4-Dihydroxynaphthalene may here be mentioned as an example.

Novolacs are also very suitable components for the mixtures. As is known, novolacs are non-selfcuring, permanently fusible, spirit-soluble or aromatic-soluble phenolic resins which result when phenol and formaldehyde in the ratio of 2:1–1.6 are warmed in the presence of acids (tartaric acid, oxalic acid, hydrochloric acid, dilute sulphuric acid and acid salts). Further details of novolacs are described, for example, in "Ullmanns Encyklopadie der technischen Chemie" ("Ullmann's Encyclopaedia of Industrial Chemistry") (1962) on pages 458 and 459.

Polycarboxylic acids to be mentioned as possible components of the mixtures according to the invention are, in particular, dicarboxylic acids or tricarboxylic acids. Suitable examples are aliphatic dicarboxylic acids with a total of 4 to 10 C atoms in the molecule, such as succinic acid, glutaric acid, adipic acid, 2,2,4-trimethyladipic acid, 2,4,4-trimethyladipic acid, pimelic acid and sebacic acid.

Furth polycarboxylic acids which can be employed for the mixtures according to the invention include aromatic and cycloaliphatic acids, such as the phthalic acids, the substituted phthalic acids and cyclohexanedicarboxylic acids.

When using the mixtures, the abovementioned amines, alcohols, phenols and carboxylic acids suitable as components for the mixtures according to the invention are essentially built into the resulting high polymer, through undergoing splitting-open of the double bonds of the maleic acid groups and addition reaction. These starting materials as well as the processes for their manufacture are known so that it is unnecessary to deal with these points in more detail here.

A basic catalyst in the mixtures according to the invention is in particular to be recommended when the reactants in the mixture are relatively unreactive or when the mixture is to be used (the high polymer is to be formed) in solution and at not very high temperatures.

Suitable basic catalysts are, according to the invention, in particular tertiary, secondary and primary amines, or amines which contain several different types of amino groups (for example mixed tertiary and secondary amines), and quaternary ammonium compounds. These amine catalysts can be either monoamines or polyamines. Where primary and secondary amines are used, monoamines are to be preferred. The following substances may be listed as examples of such amine catalysts: diethylamine, tributylamine, triethylamine, triamylamine, benzylamine, N-methylpyrrolidine, tetramethyldiaminodiphenylmethane, quinoline, N,N-diisobutylaminoacetonitrile, N,N-dibutylaminoacetonitrile, imidazole, benzimidazole and their homologues. Examples of suitable quaternary ammonium compounds which should be mentioned are benzyltrimethylammonium hydroxide and benzyltrimethylammonium methoxide.

Further suitable catalysts are alkali metal compounds, such as alkali metal alcoholates and alkali metal hydroxides. Sodium methylate is particularly suitable.

A further subject of the invention are storage-stable, hot-curable mixtures B which are suitable for the production of mouldings, impregnations, coatings, foams, adhesive bonds and the like and which are characterised in that they contain a. maleic acid derivatives of the formula I

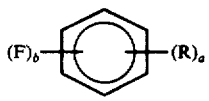

(I)

in which a denotes 1 or 2 and R denotes either the radical —NH·CO—D—CO·OH or the radical

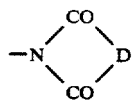

wherein D represents a divalent radical containing a carbon-carbon double bond and in which b denotes a number from 3 to 5 if $a = 1$ and denotes 3 or 4 if $a = 2$ the two radicals R are preferably in the p- or m-position to one another and b. a catalyst for the homopolymerisation, in a ratio such that there are 0.01 to 15 parts by weight of catalyst per 100 parts by weight of maleic acid derivatives.

Very suitable maleic acid derivatives for these mixtures B are the compounds of the formulae III, IV, V and VI. Suitable catalysts for the homopolymerisation are all the basic catalysts which have already been recited above, that is to say, in particular, amines, quaternary ammonium compounds and alkali metal compounds. However, further suitable catalysts are radical-forming agents, such as, for example, azodiisobutyronitrile, benzoyl peroxide, lauroyl peroxide and the like.

According to a particular embodiment of the invention, the maleic acid derivatives of the formula XI or of the formula I in the mixtures A and B can be partially replaced by fluorine-free maleic acid derivatives. In this embodiment, there should be at most 4 mols of fluorine-free maleic acid derivatives per mol of maleic acid derivatives of the formula XI or I.

The mixtures A and B according to the invention can additionally also contain the additives customary in the technology of curable plastics such as, for example, fillers, plasticisers, pigments, dyestuffs, mould release agents and flameproofing substances. As fillers they can contain, for example, glass fibres, mica, quartz powder, kaolin, colloidal silicon dioxide or metal powders and as mould release agents they can contain, for example, various waxes, zinc stearate or calcium stearate. All these additives can fundamentally also be added when processing or using the mixtures according to the invention provided the viscosity conditions then still permit sufficiently homogeneous admixture.

The mixtures A and B according to the invention can be processed in the melt or partially in the melt and partially in the solid phase, or in solution. The desired high polymers are formed when temperatures of 50° to 280° C are employed. The requisite reaction times are in general between 1 and 20 hours.

As a rule, the mixtures are used, that is to say the high polymers containing imide groups are manufactured, with simultaneous shaping to give mouldings, sheet-like structures, laminates, adhesive bonds or foams.

The following substances should be listed as examples of suitable solvents for the use of the mixtures in solution: aromatics, such as xylene and toluene; halogenohydrocarbons, such as trichloroethylene, tetrachloroethane, tetrachloroethylene and chlorobenzene; ethers, such as dioxane, tetrahydrofurane and dibutyl ether; dimethylformamide, tetramethylurea, dimethylsulphoxide and N-methylprrolidone.

When the fluorine-containing maleic acid derivatives of the formula I, according to the invention, are used in the form of curable mixtures A and B, valuable high polymers which permit a relatively wide range of variation are obtained. As compared to high polymers, the manufacture of which starts from corresponding maleic acid derivatives which do not contain fluorine, the high polymers obtainable by use of the products according to the invention show a whole series of advantages. In particular, they are of lower inflammability or, in most cases, non-inflammable. At the same time, they are more heat-stable and display improved electrical properties, reduced wettability by water and improved resistance to chemicals. Furthermore, their oil repellency is greater.

In high polymers which result from the use of the mixtures B according to the invention, these properties are very pronounced. However, particularly high quality high polymers are obtained when using mixtures A which contain maleimides of the formula III and tetrafluorophenylenediamines, especially tetrafluoro-m-phenylenediamine. The thermal decomposition point is surprisingly high, namely at about 520° C. In this property, this product resembles the known polytetrafluoroethylene.

Compared to polytetrafluoroethylene, the invention provides the advantage that neither involved sintering processes nor subsequent shaping by machining is necessary in order to shape the plastics articles. In fact, by using the invention it is possible to produce the desired shape of article, simultaneously with the manufacture of the high polymers, directly by casting, pressing or foaming.

In solving the task of the invention it was necessary, as will be explained in more detail later, to overcome a particular prejudice of those skilled in the art. It is generally known that fluorine-carbon bonds in organic molecules or molecular groups are particularly strong. This teaching can be illustrated very well by a comparison of the electronegativities of different elements (as below).

| Electronegativities of different elements (L. Pauling "The Nature of the Chemical Bond", 2nd edition, pages 58–75, Cornell University Press, Ithaca, N.Y. 1945) | |
| --- | --- |
| Fluorine | 4.0 |
| Chlorine | 3.0 |
| Carbon | 2.5 |
| Hydrogen | 2.1 |
| Nitrogen | 3.0 |

On the basis of the high electronegativity of fluorine, according to the table, one would actually have expected that the NH$_2$ groups in tetrafluorophenylenediamines and in anilines possessing 3 to 5 fluorine atoms would be of very low reactivity towards maleic anhydride and that the formation of maleamic acids or maleimides would not be possible at all. Surprisingly, however, it has now been found that even both NH$_2$ groups of the tetrafluorophenylenediamines and the NH$_2$ group of trifluoroaniline to pentafluoroaniline are sufficiently reactive towards maleic anhydrides and that therefore the preparation of the maleic acid derivatives of the formula I is realisable.

A. Preparation examples

1. Maleic acid derivative of the formula IV 18 g (1/10 mol) of tetrafluoro-m-phenylenediamine are dissolved in 200 ml of methylene chloride and slowly added dropwise at room temperature to a solution of 19.6 g (2/10 mol) of maleic anhydride in 250 ml of methylene chloride, whilst stirring. After completion of the dropwise addition, the mixture is stirred for about 30 minutes longer.

The reaction takes place in accordance with the following equation:

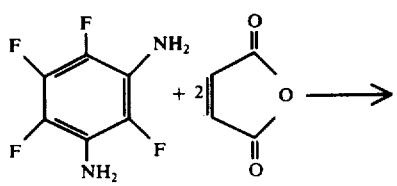

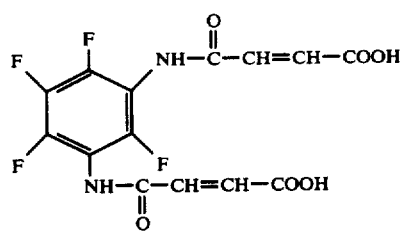

The methylene chloride is evaporated in vacuo and the intermediate product thus obtained is suspended in ether in order, as far as possible, to dissolve out incompletely converted starting materials.

After filtering off and drying, the intermediate product can be directly processed further.

| Analysis: | calculated | observed |
|---|---|---|
| C | 44.69% | 44.36% |
| H | 2.14% | 2.34% |
| N | 7.45% | 7.55% |

Melting point: 136°–138° C
Structure demonstrated by NMR.

2. Maleic acid derivative of the formula III 11.3 g (3/10 mol) of the intermediate product according to Example 1 are added in portions to a mixture consisting of 12.3 g (1.2 mols) of acetic anhydride and 1.7 g (0.22 mol) of Na acetate which has been heated to about 60° C. Heating is continued (not above 80° C), whilst stirring. All the material dissolves until, suddenly, the bis-imide crystallises out. The mixture is now allowed to cool to room temperature, whilst stirring. The bis-imide which has precipitated is suspended in a 1:1 mixture of water and alcohol, filtered off and dried. If required it can additionally be recrystallised, for example from methanol. Course of the reaction:

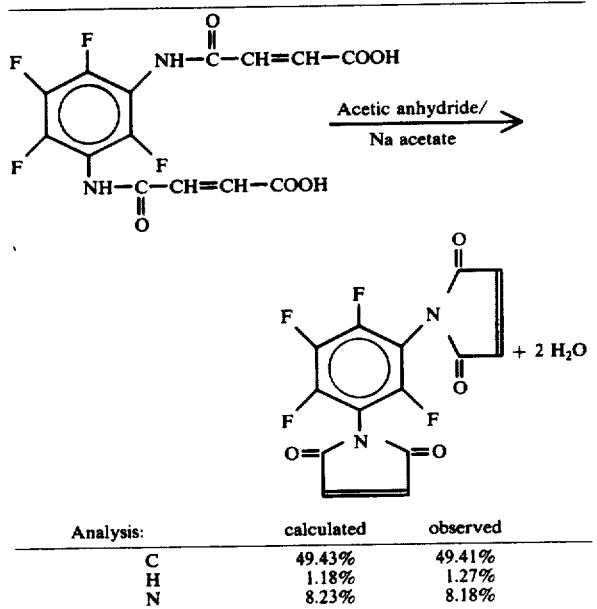

| Analysis: | calculated | observed |
|---|---|---|
| C | 49.43% | 49.41% |
| H | 1.18% | 1.27% |
| N | 8.23% | 8.18% |

Structure demonstrated by NMR.
Melting point: 197°–199° C (after recrystallisation from methanol).

3. Maleic acid derivative of the formula VI

Analogously to Example 1, 36.6 g (1/5 mol) of pentafluoroaniline in 250 ml of $CH_2Cl_2$ are reacted with a solution of 19.6 g (1/5 mol) of maleic anhydride in 250 ml of $CH_2Cl_2$. The resulting maleamic acid has a melting point of 99°–100° C.

4. Maleic acid derivative of the formula V

The procedure followed is analogous to that of Example 2, that is to say 28.1 g (1/10 mol) of the maleamic acid according to Example 3 are added in portions to a mixture of 20.4 g of acetic anhydride and 4 g of sodium acetate at about 40°–50° C. The sodium acetate can be eluted from the resulting monoimide with water/isopropanol (4:1). The imide purified in this way is filtered off and dried; if required, it can be recrystallised from isopropanol. Melting point: 105°–106° C.

| Analysis: | calculated | observed |
|---|---|---|
| C | 45.65% | 45.37% |
| H | 0.77% | 0.70% |
| F | 36.10% | 35.72% |

The NMR corresponds to the imide structure.

B. Use examples

I. The bis-imide according to Example 2 is ground and mixed with pulverulent benzimidazole (catalyst for the homopolymerisation) in the ratio of 1 0.05 of bis-imide to 0.05 mol of benzimidazole. The mixture is ground once more. This then gives a mixture B according to the invention.

The powder is fused and the melt is poured into a sheet mould. After 30 minutes' heating to 270° C (ionic polymerisation), a stable sheet is produced. The decomposition temperature is above 450° C.

II. 20 g of the mixture B according to the invention, in accordance with Example I, are dissolved in an appropriate amount of pyridine to produce a 12% strength by weight solution (% strength by weight, relative to the solution). Thereafter the solution is boiled for 2 hours under reflux. The high polymer precipitates as a glassy solid product. It has the same decomposition temperature as the high polymer obtained according to Example I.

III. The bis-imide according to Example 2 is subjected to radical polymerisation as follows: 10 g of the imide are dissolved in 100 ml of boiling toluene. 0.1 g of dilauroyl peroxide is then added. The high polymer precipitates immediately as a white powder. The decomposition temperature of the polymer is also above 450° C.

IV. The ground bis-imide according to Example 2 is mixed with pulverulent tetrafluoro-m-phenylenediamine in the molar ratio of 1:0.3 and the mixture is reground inn a ball mill. A mixture A according to the invention is obtained.

This mixture A is fused and the melt is poured into a sheet mould. After heating for 180 minutes to 270° C, a stable sheet is obtained. The decomposition temperature of the material is about 520° C.

V. The monoimide according to Example 4 is mixed with such an amount of N,N'4,4'-diphenylmethane-bis-maleimide that there are 4 mols of the latter product per mol of the monoimide (formula V). Thereafter, sufficient 4,4'-diaminodiphenylmethane is added that the mixture contains 2% by weight of this same amine catalyst. The mixture is ground. This gives a mixture B according to the invention.

The powder is fused and the melt is poured into a sheet mould. It is then heated to 205° C for 10 hours. The resulting material has the following properties.
Flexural strength (VSM 77,103)—3.1 kg/mm²
Heat distortion (ISO/R 75) —207° C.

I claim:

1. A fluorine-containing imide of the formula

in which a denotes 1 or 2 and R denotes the radical

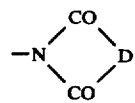

wherein D represents a divalent radical

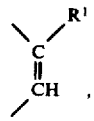

$R^1$ is hydrogen or methyl, and in which $b$ denotes a number from 3 to 5 if $a = 1$, or $b$ denotes 3 or 4 if $a = 2$, and if $a = 2$ the two radicals are preferably in the p- or in the m-position to one another.

2. A compound according to claim 1, wherein $R^1$ denotes hydrogen.

3. The compound according to claim 1, of the formula

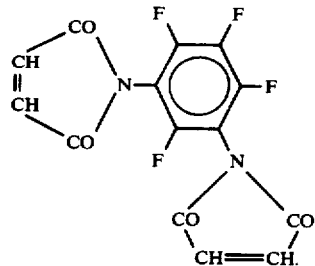

4. The compound according to claim 1, of the formula

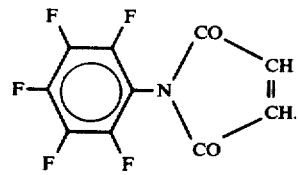

* * * * *